United States Patent
Wang

(10) Patent No.: US 9,856,452 B2
(45) Date of Patent: *Jan. 2, 2018

(54) LGR5+ SOMATIC STEM CELLS

(71) Applicant: StemBios Technologies, Inc., Monterey Park, CA (US)

(72) Inventor: James Wang, Monterey Park, CA (US)

(73) Assignee: StemBios Technologies, Inc., Monterey Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/845,952

(22) Filed: Sep. 4, 2015

(65) Prior Publication Data

US 2015/0376571 A1    Dec. 31, 2015

Related U.S. Application Data

(63) Continuation of application No. 14/097,572, filed on Dec. 5, 2013, now Pat. No. 9,155,763.

(60) Provisional application No. 61/734,106, filed on Dec. 6, 2012.

(51) Int. Cl.
| | | |
|---|---|---|
| *C12N 5/074* | (2010.01) | |
| *C12N 5/0775* | (2010.01) | |
| *A61K 35/28* | (2015.01) | |
| *A61K 35/12* | (2015.01) | |
| *A61K 35/14* | (2015.01) | |
| *A61K 35/34* | (2015.01) | |
| *A61K 35/35* | (2015.01) | |

(52) U.S. Cl.
CPC ............ *C12N 5/0607* (2013.01); *A61K 35/12* (2013.01); *A61K 35/14* (2013.01); *A61K 35/28* (2013.01); *A61K 35/34* (2013.01); *A61K 35/35* (2013.01); *C12N 5/0663* (2013.01)

(58) Field of Classification Search
None
See application file for complete search history.

(56) References Cited

U.S. PATENT DOCUMENTS

| | | |
|---|---|---|
| 6,004,807 A | 12/1999 | Banchereau et al. |
| 6,440,735 B1 | 8/2002 | Gaeta |
| 6,716,422 B1 | 4/2004 | Gajewski et al. |
| 6,916,654 B1 | 7/2005 | Sims et al. |
| 6,986,887 B2 | 1/2006 | Lawman et al. |
| 7,316,932 B2 | 1/2008 | Woodside |
| 7,575,921 B2 | 8/2009 | Vacanti et al. |
| 7,651,690 B2 | 1/2010 | Jensen et al. |
| 7,972,847 B2 | 7/2011 | Kalinski |
| 8,158,758 B2 | 4/2012 | Gurney |
| 8,206,907 B2 | 6/2012 | Milstein et al. |
| 8,337,858 B2 | 12/2012 | Scoglio et al. |
| 8,394,630 B2 | 3/2013 | Wang et al. |
| 8,673,296 B2 | 3/2014 | Karlsson-Parra et al. |
| 2002/0115059 A1 | 8/2002 | Terada et al. |
| 2003/0161817 A1 | 8/2003 | Young et al. |
| 2004/0136967 A1 | 7/2004 | Weiss et al. |
| 2004/0175823 A1 | 9/2004 | Vacanti et al. |
| 2005/0255588 A1 | 11/2005 | Young et al. |
| 2006/0035373 A1 | 2/2006 | Zhang et al. |
| 2006/0040392 A1 | 2/2006 | Collins et al. |
| 2006/0171931 A1 | 8/2006 | Rudnicki et al. |
| 2006/0252150 A1 | 11/2006 | Cheng |
| 2007/0190023 A1 | 8/2007 | Battista et al. |
| 2008/0152665 A1 | 6/2008 | Leclerc et al. |
| 2008/0305079 A1 | 12/2008 | Chen |
| 2009/0004661 A1 | 1/2009 | Shetty |
| 2009/0104158 A1 | 4/2009 | Young et al. |
| 2009/0104160 A1 | 4/2009 | Young et al. |
| 2009/0155225 A1 | 6/2009 | Ratajczak et al. |
| 2009/0186334 A1 | 7/2009 | Young et al. |
| 2010/0081199 A1 | 4/2010 | Slukvin et al. |
| 2010/0183570 A1 | 7/2010 | Wang et al. |
| 2011/0305673 A1 | 12/2011 | Spees |
| 2012/0021482 A1 | 1/2012 | Zuba-Surma et al. |
| 2012/0028355 A1 | 2/2012 | Sato et al. |
| 2012/0034194 A1 | 2/2012 | Wang |
| 2012/0177670 A1 | 7/2012 | Wang |
| 2013/0095077 A1 | 4/2013 | Wang |
| 2013/0189327 A1 | 7/2013 | Ortega et al. |
| 2013/0236485 A1 | 9/2013 | Wang |
| 2014/0161774 A1 | 6/2014 | Wang |
| 2014/0219952 A1 | 8/2014 | Cameron |
| 2014/0377760 A1 | 12/2014 | Wang et al. |
| 2016/0166611 A1 | 6/2016 | Wang |

FOREIGN PATENT DOCUMENTS

| | | |
|---|---|---|
| CN | 102008650 | 4/2011 |
| EP | 1632563 | 3/2006 |
| EP | 2818544 A1 | 12/2014 |
| JP | H0391491 A | 4/1991 |

(Continued)

OTHER PUBLICATIONS

Aiuti, et al., "Expression of CXCR4, the Receptor for Stromal Cell-derived Factor-1 on Fetal and Adult Human Lympho-hematopoietic Progenitors", European Journal of Immunology. Published 1999. Wiley-VCH Verlag GmbH, Weinheim. pp. 1823-1831.

Adyama et al. "Stromal cell CD9 regulates differentiation of hematopoietic stem/progenitor cells" Hematopoiesis, Blood, 93(8):2586-2594, 1999.

Banerjee et al. "An antibody to the tetraspan membrane protein CD9 promotes neurite formation in a partially α3β1 integrin-dependent manner" The Journal of Neuroscience 17(8):2756-2765, 1997.

Barker, et al., "Identification of stem cells in small intestine and colon by marker gene Lgr5", Articles, Nature Publishing Group, Oct. 2007.

Barker, et al., "Lgr5+ve Stem Cells Drive Self-Renewal in the Stomach and Build Long-Lived Gastric Units in Vitro", Cell Stem Cell, vol. 6, Jan. 2010.

(Continued)

*Primary Examiner* — Daniel C Gamett
(74) *Attorney, Agent, or Firm* — Cesari and McKenna, LLP

(57) ABSTRACT

Described is an isolated somatic stem cell that is 2 to less than 6 micrometer in size and Lgr5+. Methods of preparing and using the cell are also described.

20 Claims, No Drawings

(56) References Cited

FOREIGN PATENT DOCUMENTS

| | | |
|---|---|---|
| JP | 2001/128660 A | 5/2001 |
| WO | WO-99/26639 | 6/1999 |
| WO | WO-2006/028723 | 3/2006 |
| WO | WO-2006/070370 | 7/2006 |
| WO | WO-2007/026353 | 3/2007 |
| WO | WO-2007/087367 | 8/2007 |
| WO | WO-2007/100845 | 9/2007 |
| WO | WO-2008/148105 | 12/2008 |
| WO | WO-2009/012357 | 1/2009 |
| WO | WO-2009/061024 | 5/2009 |
| WO | WO-2009/959032 | 5/2009 |
| WO | WO-2009/136283 | 11/2009 |
| WO | WO-2010/039241 | 4/2010 |
| WO | WO-2010/083203 | 7/2010 |
| WO | WO-2010/099044 | 9/2010 |
| WO | WO-2011/137540 | 11/2011 |
| WO | WO-2012/019002 | 2/2012 |
| WO | WO-2013/049459 | 4/2013 |

OTHER PUBLICATIONS

Battula, et al. "Prospective isolation and characterization of mesenchymal stem cells from human placenta using a frizzled-9-specific monoclonal antibody", Differentiation, 2008, vol. 76, pp. 326-336.

Battula, et al., "Human placenta and bone marrow derived MSC cultured in serum-free, b-FGF-containing medium express cell surface frizzled-9 and SSEA-4 and give rise to multilinelage differentiation", Differentiation, Spinger Verlag, DE, col. 75, No. 4, Apr. 2007.

Bellato, et al., Pain Research and Treatment vol. 2012 pp. 1-7.

Buhring et al. "Novel markers for the prospective isolation of human MSC" Ann. N.Y. Acad. Sci. 1106:262-271, 2007.

Cai, et al., (NeuroMolecular Medicine, 2002, vol. 2, pp. 233-249).

Cui et al. "Spatial distribution and initial changes of SSEA-1 and other cell adhesion-related molecules on mouse embryonic stem cells before and during differentiation" Journal of Histochemistry & Cytochemistry, 52(11):1447-1457, 2004.

Fickert et al. "Identification of subpopulations with characteristics of mesenchymal progenitor cells from human osteoarthritic cartilage using triple staining for cell surface markers" Arthritis Research & Therapy, 6(5):R422-R432, 2004.

Furusawa et al. "Embryonic stem cells expressing both platelet endothelial cell adhesion molecule-1 and stage-specific embryonic antigen-1 differentiate predominantly into epiblast cells in a chimeric embryo" Biology of Reproduction, 70:1452-1457 (2004).

Gang et al. Prospective isolation of MSC with SSEA-4; Blood First Edition Paper, prepublished on line Oct. 24, 2006: DOI 10.1182/blood-2005-11-010504.

Gang et al. "SSEA-4 identifies mesenchymal stem cells from bone marrow", Stem Cells in Hematology, Blood, 109(4):1743-1751, 2007.

Glazar et al. "IgSF8 (EWI-2) and CD9 in fertilization: Evidence of distinct functions for CD9 and a CD9-associated protein in mammalian sperm-egg interaction" Reprod Fertil Dev. 21(2):293-303, 2009.

Huang et al. "Isolation and characterization of cell subpopulation with stem cell properties in human and monkey intervertebral disc (IVD)" EMC Journal 2009 p. 28.

Hung, et al., "Isolation and characterization of size-sieved stem cells from human bone marrow", Stem Cells, Alphamed Press, vol. 20, No. 3, 2002.

Hur, "Highly Angiogenic CXCR4 and CD31 monocyte subset derived from 3D culture of human peripheral blood", Biomaterials, 2013, pp. 1929-1941.

Jaks, et al, "Lgr5 marks cycling, yet long-lived, hair follicle stem cells," Nature Genetics, vol. 40, No. 11, 1291-1299 (2008).

Kadam et al. "Islet neogenesis from the constitutively nestin expressing human umbilical cord matrix derived mesenchmal stem cells" Islets 2:2, 112-120, 2010.

Kim et al. "Role of CD9 in proliferation and proangiogenic action of human adipose-derived mesenchymal stem cells" Cell and Molecular Physiology Eur. J. Physiol 455:283-296, 2007.

Kim, et al., "Generation of human Induced pluripotent stem cells from osteoarthritis patient-derived synovial cells", Arthritis and Rheumatism, 6(10):3010-2021 (2011).

Kogler, et al., "A new human somatic stem cell from placental cord blood with intrinsic pluripotent differentiation potential", Journal of Experimental Medicine, vol. 200, No. 2, 2004.

Kucia et al. "Evidence that very small embryonic like (VSEL) stem cells are mobilized into peripheral blood" Stem Cells Express, published online Jun. 5, 2008; doi:10.1634/stemcells.2007-0922 p. 1-23.

Kucia, et al., "A population of very small embryonic-like (VSEL) CXCR4+SSEA=1+Oct4+ stem cells identified in adult bone marrow", Leukemia, vol. 20, 2006.

Kucia, et al., "Morphological and molecular characterization of novel population of CXCR4+ SSEA=4+ very small embryonic-like cell purified from human cord blood-preliminary report", Leukemia, vol. 21, 2007.

Kucia, et al., "Physiological and pathological consequences of identification of very small embryonic like (VSEL) stem cells in adult bone marrow", Journal of Physiology and Pharmacology, 2006, 57, Supp 5, 5-18.

Lian et al. "Establishing clonal cell lines with endothelial-like potential from CD9hl, SSEA-1 Cells in embryonic stem cell-derived embryoid bodies" PLoS ONE 1:(e6)1-10, 2006.

Lindvall, et al., J. Clin Invest. Jan 4, 2010; 120(1): 29-40.

Magnus, et al., Philos Trans R Soc Lond B Biol Sol. Jan. 12, 2008; 363 (1489): 9-22.

Meng et al. "Endometrial regenerative cells: A novel stem cell population" Journal of Translational Medicine, 5:(57)1-10, 2007.

Meregalli, et al., BioDrugs 2010, vol. 24, Issue 4, pp. 237-247.

Muller et al. "A novel embryonic stem cell like derived from the common marmoset monkey (callithrix jacchus) exhibiting germ cell-like characteristics" Human Reproduction, 24(6):1359-1372, 2009.

Negroni, et al., Expert Opin Biol Ter. Feb. 2011; 11(2):157-176.

Noggle, et al., "Notch signaling is inactive but inducible in human embryonic stem cells", Stem Cells, vol. 24, No. 7, 2006.

Oka et al. "CD9 is associated with leukemia inhibitory factor-mediated maintenance of embryonic stem cells" Molecular Biology of the Cell, 13:1274-1281, 2002.

Prowse et al. "Multiplexed staining of live human embryonic stem cells for flow cytometric analysis of pluripotency markers" Stem Cells and Development, 18(8): 1135-1139, 2009.

Ratajczak, et al., "Very small embryonic-like (VSEL) stem cells: purification from adult organs, characterization, and biological significance", Stem Cell Reviews, vol. 4, No. 2, 2008.

Sackstein, et al., "Ex vivo glycan engineering on cd44 programs human multipotent mesenchymal stromal cell trafficking to bone", Nat, Med., vol. 14, pp. 181-187, 2008.

Sato, et al., "Paneth cells constitute the niche for Lgr5 stem cells in intestinal crypts", Nature, vol. 469, Jan. 2011.

Shinohara et al. "CD9 is a surface marker on mouse and rat male germline stem Cells", Biology of Reproduction, 70:70-75, 2004.

Shmilovici "Mammalian spore-like cells—A reservoir of spare parts for old-age?" Medical Hypotheses, 2007, 68:767-769.

Stint et al. "Primitive stem cells residing in the skeletal muscle of adult pigs are mobilized into the peripheral blood after trauma" The American Surgeon, 73:1106-1110, 2007.

Tole et al. "Distribution of CD9 in the developing and mature rat nervous system" Developmental dynamics 197:94-106, 1993.

Tourandre, et al., Arthritis & Rheumatism vol. 64, No. 2, pp. 533-541, 2012.

Trubiani et al. "Expression profile of the embryonic markers nanog. OCT-4, SSEA-1, SSEA-4 , and frizzled-9 receptor in human periodontal ligament mesenchymal stem cells" 2010 DOI.10.1002/jcp. 22203p. 1-14.

Vacanti et al. "Identification and initial characterization of spore-like cells in adult mammals" Journal of Cellular Biochemistry, 80:455-460, 2001.

(56) References Cited

OTHER PUBLICATIONS

Wojakowski et al "Very Small Embryonic-Like Stem Cells in Cardiovascular Repair" Pharmacology & Therapeutics vol. 129, pp. 21-28. 2011.
Young "Existence of Reserve quiescent stem cells in adults, from amphibians to humans" Immunol., 280:71-109, 2004.
Young et al. "Cancer gene mechanisms and gene therapy" Reviews, Minerva Biotec. 17:55-63, 2005.
Yu, et al., Liver Transpl. Jan. 2012; 18 (1): 9-21.
Zuba-Surma, et al., "'Small stem cells' in adult tissues: Very small embryonic-like stem cells stand up!", Cytometry Part A, vol. 75A, No. 1, 2009.
Zulewski et al. "Multipotential nestin-positive stem cells isolated from adult pancreatic islets differentiate ex vivo into pancreatic endocrine, exocrine, and hepatic phenotypes" Diabetes, 50:521-533, 2001.
http://stemcells.nih.gov/info/glossary.asp.
Abeyta, et al., 2004, Human Molecular Genetics, vol. 13, No. 6, pp. 601-608.
Allergrucci, et al., 2006, Human Reproduction Update, Vol. Advance Access published on Aug. 26, 2006, p. 1-18.
Amit, et al., "Feeder Layer-and Serum-Free Culture of Human Embryonic Stem Cells", Biology of Reproduction, 2004, vol. 70, pp. 837-845.
Arechaga et al.; "Characterisation of new intracellular membranes in Escherichia coli accompanying large scale over-production of the b subunit of F1F0 ATP synthase"; FEBS Letters 482:215-219 (2000).
Bizzetto et al.; "Outcomes after related and unrelated umbilical cord blood transplantation for hereditary bone marrow failure syndromes other than fanconi anemia"; Haematologica 96(1)134-141 (2011).
Dolcetti, et al., "Myeloid-Derived Suppressor Cell Rolse in Tumor-Related Inflammation", Cancer Letters; 267:216-225 (2008).
Fitton, et al., "Therepaies from Fucoidan; Multifunction Marine Polymers", Marine Drugs, vol. 9, No. 12, Dec. 30, 2011, pp. 1731-1760.
Gabrilovich, et al., "Myeloid-Derived-Suppressor Cells as Regulators of the Immune System", Nat. Rev. Immunol.; 9(3):162-176 (2009).
Hamman, et al. 2005, Biodrugs, vol. 19, No. 3, pp. 165-177.
Haraguchi, et al., "CD13 is a therapeutic target in human liver cancer stem cells", Jornal of Clinical Investigation, vol. 120, No. 9, Sep. 1, 2010, pp. 3326-3339.
Irhimeh, et al., "Fucoidan ingestion increases the expression of CXCR4 on human CD34 +cells", Experimental Hematology, vol. 35, No. 6, Jun. 1, 2007, pp. 989-994.
Jensen, et al., "Mobilization of human CD34<+>CD133<+> and CD34<+>CD133<−> stem cells in vivo by consumption of an extract from Aphanizomenon flos-aquae-related to modulation of CXCR4 expression by an L-selectin ligand?", Cardiovascular Revascularization Medicine, Elsevier, NL, vol. 8, No. 3, Aug. 29, 2007 pp. 189-202.
Li, et al., 2009, Transplant Immunology, vol. 21, pp. 70-74.
LV, et al., "Concise Review: The Surface Markers and Identity of Human Mesenchymal Stem Cells", Stem Cells vol. 32, pp. 1408-1419, 2014.
Ostrand-Rosenberg, et al., "Myeloid-Derived Suppressor Cells: Linking Inflammation and Cancer", J. Immunol.; 182:4499-4506 (2009).
Sato, et al., 2003, Developmental Biology, vol. 260 p. 404-413.
Schuldiner, et al., "Effects of eight growth factors on the differentiation of cells derived from human embryonic stem cells", PNAS, 2000, vol. 97, pp. 11307-11312.
Serafini, et al., "Myeloid Suppressor Cells in Cancer: Recruitment, Phenotype, Properties, and Mechanisms of Immune Suppression", Seminars in Cancer Biology; 16:53-65 (2006).
Sharp III, et al., 2014, Frontiers in Oncology, vol. 4, Article 299, p. 1-13.
Sinha et al.; "Prostaglandin E2 promotes tumor progression by inducing myeloid-derived suppressor cells"; Cancer Res, 67(9):4507-4513 (2007).
Sprangers, et al., 2008, Kidney Immunology, vol. 74, pp. 14-21.
Stemrx Bio Science, "Get Rid of Ankylosing Spondylitis with Stem Cell Treatment and Applied Therapies", 2013.
Sweeney, et al., "Mobilization of stem/progenitor cells by sulfated polysaccharides does not require selectin presence", Proceedings of the National Academy of Sciences, National Academy of Sciences, U.S., vol. 97, No. 12, Jun. 6, 2000 pp. 6544-6549.
Taha, 2010, Current Stem Cell Research & Therapy, vol. 5, pp. 23-36.
Talmadge, "Pathways Mediating the Expansion and Immunosuppressive Activity of Myeloid-Derived Suppressor Cells and Their Relevance to Cancer Therapy", Clin. Cancer Res.; 13918:5243-5248 (2007).
Tennis, et al. Neoplasia 2012; 12:244-53.
Tu et al.; "Overexpression of interleukin-1 beta induces gastric inflammation and cancer and mobilizes myeloid-derived suppressor cells in mice"; Cancer Cell, 14(5):408-419 (2008).
Wang, et al., "Effects and Safety of Allogenic Mecenchymal Stem Cell Intravenous Infusion in Active Ankylosing Spondylitis Patients Who Failed NSAIDs: A 20-Week Clinical Trial", Cell Transplantation, vol. 23, pp. 1293-1303, 2013.
Wu, et al., 2012, Ageing Research Reveiws, vol. 11, pp. 32-40.
Young et al.: "Adult-derived stem cells and their potential for use in tissue repair and molecular medicine"; J. Cell. Mol. Med., 9(3):753-769 (2005).
Zhao, et al. "A human peripheral blood monocyt-derived subset acts as pluripotent stem cells", Proceedings of the National Academy of Sciences, National Academy of Sciences, vol. 100, No. 5, pp. 2426-2431, Mar. 4, 2003.
Hsu, et al., "Characterization of Two LGR Genes Homologous to Gonadotropin and Thyrotopin Receptors with Extracellular Leucine-Rich Repeats and a G Protein-Coupled, Seven-Transmembrane Region", Mol. Endocrinology, 1998, vol. 12, No. 12, pp. 1830-1845).
Ratajczak, et al., "Bone Marrow—Home of Versatile Stem Cells", Transfuion Medicine and Hemotherapy 2008;35:248-259.
Karaoz et al "Characterization of Mesenchymal Stem Cells from Rat Bone Marrow: Ultrastructural Properties, Differentiation Potential and Immunophenotypic Markers" Histochemistry and Cell Biology vol. 132, pp. 533-546, 2009.
Phadnis et al "Mesenchymal Stem Cells Derived from Bone Marrow of Diabetic Patients Portrait Unique Markers Influenced by the Diabetic Microenvironment" The Review of Diabetic Studies vol. 6, pp. 260-270, 2009.
Zhao et al "Embryonic Stem Cell Markers" Molecules vol. 17, pp. 6196-6236, 2012.
Choi, "Adult Stern Cell Therapy for Autoimmune Disease", International Journal of Stem Cells vol. 2, No. 2, 2009.

LGR5+ SOMATIC STEM CELLS

CROSS REFERENCE TO RELATED APPLICATIONS

This application is a continuation of U.S. application Ser. No. 14/097,572, filed on Dec. 5, 2013, which claims priority to U.S. Provisional Application No. 61/734,106, filed on Dec. 6, 2012. The contents of the prior applications are incorporated herein by reference in their entirety.

BACKGROUND

Stem cells are pluripotent or totipotent cells that can differentiate in vivo or in vitro into many or all cell lineages. Due to their pluripotency, embryonic stem (ES) cells hold great promise for treating degenerative or inherited diseases. Yet, ethical considerations have hampered the use of human ES cells. Stem cells of a non-embryonic origin would circumvent this obstacle. These adult stem cells have the same capability for differentiation as do ES cells.

Multipotent adult progenitor cells from bone marrow have been isolated that can differentiate into ectoderm, mesoderm and endoderm. Other types of cells, including marrow-isolated adult multi-lineage inducible cells and single cell clones derived from bone marrow also have the same multi-potential ability for differentiation. Such multipotent somatic cells are difficult to obtain, culture, and expand.

Thus, there is a need for adult somatic stem cells that can be easily isolated and maintained.

SUMMARY

The details of one or more embodiments are set forth in the description below.

Provided is an isolated somatic stem cell that is 2.0 to less than 6.0 micrometer in size and Lgr5 positive.

Also provided is a method of preparing a population of somatic stem cells. The method includes the steps of obtaining from a subject a tissue sample containing a plurality of cells, incubating the sample with EDTA or heparin in a container until the sample is separated into an upper layer and a lower layer, collecting the upper layer, and isolating from the upper layer a population of somatic stem cells that are 2 to less than 6 micrometers in size and Lgr5+.

In one aspect, a population of somatic stem cells is prepared by the above-described method.

In another aspect, described is a cell bank containing a plurality of populations of somatic stem cells, the plurality of populations being prepared from blood or bone marrow samples of different subjects by the method described above.

Additionally, a method is provided for treating a disorder or condition. The disorder or condition is a muscular degenerative disorder, a neurodegenerative disorder, a muscle injury, a cancer or an autoimmune disease. The method comprises administering to a subject in need thereof an effective amount of the somatic stem cells prepared by the method set forth above.

The details of one or more embodiments are set forth in the description below. Other features, objects, and advantages of the invention will be apparent from the description and from the claims.

DETAILED DESCRIPTION

Described herein are SB cells, which are adult stem cells that are less than 6.0 μm in size and include SB-1 cells, which stain positive for CD9. i.e., CD9+, and also CD9− cells. See US2012/0034194. Within the CD9− cell population is a unique subpopulation of cells which are 2.0 to less than 6.0 μm in size and Lgr5+. Lgr5+ SB cells are also Oct4+ and Nanog+, as well as CD133−, CD66e−, Sox2−, CD4−, CD8−, CD9−, CD10−, CD11−, CD16−, CD17−, CD18−, CD19−, CD20−, CD21−, CD31−, CD42−, CD63−, CD34−, Lin−, CD38−, CD90−, CD45−, and CD349−.

Lgr5+ SB cells are pluripotent or totipotent stem cells prepared from non-embryonic origins. Lgr5+ SB cells can be differentiated into cell types associated with the three embryonic germ layers, namely, ectoderm, endoderm, and mesoderm. In one embodiment, the cells are non-adherent. It therefore can be used to regenerate differentiated, functional cells in treating various degenerative disorders or tissue damage. As shown in the examples below, the population can be easily prepared, maintained, and expanded in vitro, and induced to differentiation using routine technical approaches. In addition, after grafting the stem cells in the population into an animal subject (e.g., a mouse), there is no evidence of malignant growth. Containing a normal chromosomal complement, these stem cells are lineage-uncommitted and can form all somatic (non-reproductive) cells of the body. They can also form the reproductive gametes sperm and/or ovum, and cells and tissues of the embryonic and fetal portions of the placenta. These stem cells are responsive to lineage-induction agents, proliferation agents, and differentiation inhibitory agents. Due to these advantages, they represent an alternative to other stem cells.

The term "stem cell" herein refers to a cell that is totipotent or pluripotent, i.e., capable of differentiating into a number of final, differentiated cell types. Totipotent stem cells typically have the capacity to develop into any cell type. Totipotent stem cells can be both embryonic and non-embryonic in origin. Pluripotent cells are typically cells capable of differentiating into several different, final differentiated cell types. Unipotent stem cells can produce only one cell type, but have the property of self-renewal which distinguishes them from non-stem cells. These stem cells can originate from various tissue or organ systems, including blood, nerve, muscle, skin, gut, bone, kidney, liver, pancreas, thymus, and the like.

The stem cells disclosed herein are substantially pure. The term "substantially pure", when used in reference to stem cells or cells derived therefrom (e.g., differentiated cells), means that the specified cells constitute the majority of cells in the preparation (i.e., more than 20%, 30%, 40%, 50%, 60%, 70%, 80%, 90%, or 95%). Generally, a substantially purified population of cells constitutes at least about 70% of the cells in a preparation, usually about 80% of the cells in a preparation, and particularly at least about 90% of the cells in a preparation (e.g., 95%, 97%, 99% or 100%). As such, a method described herein provides the advantage that a substantially pure population of Lgr5+ SB cells can be obtained without contamination by other cell types.

Lgr5+ SB cells can be isolated either from a human or from a non-human. Examples of a non-human source include, but are not limited to non-human primates, dogs, rodents, guinea pigs, cats, horses, cows, sheep, and pigs. In other words, sources of Lgr5+ SB cells include pet animals, farm animals, experimental animals, and disease-model animals. In one embodiment, Lgr5+ SB cells are isolated from a human.

Lgr5+ SB cells can be isolated from a tissue such as blood, bone marrow, skeletal muscle, or adipose tissue. In one embodiment, Lgr5+ SB cells are isolated from blood. In a preferred embodiment, the blood donor is human.

Lgr5+ SB cells can be isolated from a tissue sample by the following method. First, cells in the tissue sample are incubated with a divalent cation chelating agent (e.g., EDTA, EGTA, and sodium citrate) or heparin in a container until the sample is separated into an upper layer and a lower layer. The incubation can be performed for 6 to 48 hours at a temperature of 4° C. Preferably, the incubation is performed for 48 hours at 4° C.

The upper layer produced by the above incubating step is collected, and a population of somatic stem cells that are 2 to less than 6 micrometers in size and Lgr5+ is isolated from this upper layer.

The isolation of Lgr5+ SB cells from the upper layer can be conducted by methods based on cell size (e.g., centrifuging and filtering) or those based on cell surface markers (e.g., flow cytometry).

The incubating step can be performed by incubating the sample with heparin, and, in between the collecting step and the isolating step, the collected upper layer is incubated with EDTA.

The method can further include, after the upper layer has been collected, incubating it with ADP so as to allow platelets/microparticles to precipitate for further enrichment of SB somatic stem cells. In addition, it can also include incubating the upper layer obtained from a heparin-treated sample with a divalent cation chelating agent to activate the cell cycle of the stem cells from G0 into G1.

In an embodiment where the tissue sample is skeletal muscle or adipose tissue, the cell isolation method can include, between the obtaining step and the incubating step, digesting the tissue sample with a collagenase to release individual cells from the extracellular matrix.

To confirm that this isolated population indeed contains Lgr5+ SB cells, one can examine a number of characteristics, including (1) sizes of cells in suspension that between 2.0 to less than 6.0 μm, e.g., 2.0 to 5.0 μm; and (2) cell surface markers. Antibodies against cell surface markers, such as Lgr5, can be used. They can be conjugated with suitable labels, such as fluorescein isothiocyanate (FITC), phycoerythrin (PE), or quantum dots. Lgr5+ SB cells can be further enriched using flow cytometry.

The isolated or enriched cells can then be tested by standard techniques. To confirm the differentiation potential of Lgr5+ SB stem cells, they can be induced to form, for example, neuro-glial cells, osteocyte, and adipocyte by methods known in the art. For example, these cells can be passed and cultured to confluence, shifted to an osteogenic medium or an adipogenic medium, and incubated for a suitable period of time (e.g., 3 weeks). The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, these cells can be incubated in a neurogenic medium for a suitable duration (e.g., 7 days), and then subjected to serum depletion and incubation of β-mercaptoethanol. After differentiation, they exhibit the morphology of refractile cell body with extended neuritelike structures arranged into a network. RT PCR and immunocytochemical stain of lineage specific markers are further conducted to confirm neural differentiation. Examples of the markers include neuron specific class III β-tubulin (Tuj-1), neurofilament, and GFAP.

Alternatively, to confirm the identity of the isolated cells, one can take advantage of the discovery that SB cells, in response to a divalent cation chelating agent (EDTA), proliferate quickly. To that end, one can culture the isolated cells with, e.g., EDTA. Under that condition, Lgr5+ SB cells will proliferate.

Lgr5+ SB cells can be further propagated in a non-differentiating medium culture for more than 10, 20, 50, or 100 population doublings without indications of spontaneous differentiation, senescence, morphological changes, increased growth rate, or changes in ability to differentiate into neurons. These stem cells can be stored by standard methods before use.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division.

The term "terminal differentiation" refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with withdrawal from the cell cycle and cessation of proliferation. The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

The above-described Lgr5+ SB cells can be used in a variety of ways.

Cell Banking

A plurality of populations of Lgr5+ SB cells can be used to generate a cell bank. The populations are separately prepared from bodily fluid samples, e.g., blood and bone marrow, from different subjects by the above-described method. An Lgr5+ SB cell population in the bank or library can be derived from a healthy subject or subject having known disease state or disease symptom. These stem cells can be human cells or non-human cells.

The bank can be produced by harvesting Lgr5+ SB cell populations separately from different subjects; characterizing the Lgr5+ SB cell populations to obtain at least one predetermined characteristic for each, and cataloguing each of the Lgr5+ SB cell populations according to the at least one predetermined characteristic. Examples of the characteristic include a subject's name, gender, physical conditions (including genetic disorders and MHC information). To produce the bank, one can further expand the Lgr5+ SB cell populations.

A cell bank or library having cells differentiated from the above-described stem cells can also be generated. Examples of cells differentiated from the stem cells include brain cells, neurons, astrocytes, glial cells, T cells, B cells, cartilage cells, bone cells, pancreatic islet cells, fat cells, heart cells, liver cells, kidney cells, lung cells, muscle cells, and eye cells. The subjects may be human or nonhuman vertebrates. The stem cells can be derived from any mammalian organism, such as human, mouse, rabbits, cows, pigs, and the like.

The cells in the bank or library are catalogued according to predetermined characteristics, including phenotypic information, morphological characteristics, differentiation profile, blood type, major histocompatibility complex, disease state of donor, or genotypic information (e.g. single nucleated polymorphisms (SNPs) of a specific nucleic acid sequence associated with a gene, or genomic or mitochondrial DNA). The cells are stored under appropriate conditions (typically by freezing) to keep the stem cells alive and functioning. Cataloguing may constitute creating a centralized record of the characteristics obtained for each cell population, such as, but not limited to, an assembled written record or a computer database with information inputted therein. Essentially, this embodiment pertains to the production of a stem cell bank. The stem cell bank facilitates the selection from a plurality of samples of a specific stem cell sample suitable for a user's needs. Thus, another embodiment of the subject invention pertains to a stem cell bank comprising a plurality of stem cells samples obtained from separate sources and which are characterized and catalogued according to at least one predetermined characteristic. An additional embodiment pertains to a method of establishing a stem cell bank comprising collecting stem samples from multiple sources; cataloguing the samples according to at least one predetermined characteristic and storing the cells under conditions that keep cells viable.

Within the scope of this invention is a stem cell banking system containing a plurality of stem cell populations disposed in individual containers under conditions to keep the stem cell populations viable; a database computer comprising at least one processing module, a display, and a storage medium comprising information of at least one characteristic for each stem cell population; and at least one program code module for causing the information to be viewable on said display upon command by a user. In a specific embodiment, the invention features a stem cell banking system where stem cell populations have stem cells obtained from subjects who have a disease condition. The disease condition may include the above-described degenerative diseases. Lgr5+ SB cell populations are harvested from different subjects having different diseases, and the stem cells are characterized. The characteristic(s) is/are inputted into the database computer. In addition, or alternatively, cells are characterized based on a specific phenotype not necessarily associated with a disease condition. For example, liver cells can be characterized based on their ability to metabolize certain compounds such as caffeine, alcohol, drug agents, etc. to study genetic bases of such different metabolism abilities, or underlying physiology associated therewith. Other types of cells can be characterized based on functional and/or morphological phenotypes.

In certain embodiments, cells differentiated from an Lgr5+ SB cell population may be subjected to conditions to influence differentiation or dedifferentiation through introduction of engineered vectors, or other genetic material. Dedifferentiation comprises the manipulation of a cell such that it takes on the properties of a less differentiated cell.

The stem cell libraries of the invention can be used to screen for agents or compounds that may be used to treat degenerative disorders, cancer or immune disorders in the manner described above. The libraries are suitable for high throughput screening and are useful for identifying agents that are specifically effective for a particular subject. For a high throughput screening, stem cells can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the screening methods of the invention provide a means to screen one, a few, or a large number of test agents in order to identify an agent that can alter a function of stem cells, for example, an agent that induces the cells to differentiate into a desired cell type, or that prevents spontaneous differentiation, for example, by maintaining a high level of expression of regulatory molecules.

Universal Donor Cells

The above-described stem cells can be genetically engineered to generate histocompatible donor cells or tissues for transplantation. More specifically, the stem cells described herein can be genetically engineered to not express on their surface class II MHC molecules. More preferably, the cells are engineered to not express substantially all cell surface class I and class II MHC molecules. As used herein, the term "not express" mean either that an insufficient amount is expressed on the surface of the cell to elicit a response or that the protein that is expressed is deficient and therefore does not elicit a response.

The MHC molecules refer to HLA molecules, specifically of classes HLA A, B and C, and class II HLA DP, DQ, and DR, and their subclasses. This terminology is generally construed as specific to the human MHC, but is intended herein to include the equivalent MHC genes from the donor cell species, for example, if the cells are of porcine origin, the term HLA would refer to the equivalent porcine MHC molecules, whether MHC I or II. When the class II MHC molecules are removed, CD4+ T-cells do not recognize the genetically engineered endothelial cells; when both the class I and class II MHC molecules are removed neither CD4+ nor CD8+ cells recognize the modified cells.

The genetic modification performed on the stem cells can include 1) disrupting the endogenous invariant chain gene which functions in the assembly and transport of class II MHC molecules to the cell surface and loading of antigenic peptide, and 2) disrupting the endogenous $\beta_2$-microglobulin gene ($\beta_2$M gene), which codes for a protein required for the cell surface expression of all class I MHC molecules. Alternatively, just the invariant chain gene is disrupted. Invariant chain is believed to be required for the insertion of antigenic peptide fragments into the MHC class II molecule. Together, the antigenic peptide and MHC are recognized by T cells. In the absence of antigenic peptide, T cell recognition is not normally obtained, nor is the MHC class II molecule folded properly. Thus, in cells lacking invariant chain, presentation of peptide will be abrogated and even if minuscule amounts of cell surface MHC are obtained, they may be devoid of peptide and therefore, non-immunogenic.

Disruption of these genes can be accomplished by means of homologous recombination gene targeting techniques. These techniques are well known in the art. See e.g., U.S. Pat. Nos. 6,916,654 and 6,986,887.

Screening Methods

The above-described Lgr5+ SB stem cells can be used in screening assays to identify drugs that can affect a particular cell type in a manner indicating that the drug can be useful for treating a disorder associated with the cell type. For example, one can use the stem cells in a method for identifying a drug candidate for treating a disease (e.g., a degenerative disease). The method includes the steps of contacting a test compound with the stem cells and determining the expression level of a polypeptide that is down-regulated in the disease. The expression level in the presence of the test compound, if higher than that in the absence of the compound, indicates that the compound is a candidate for treating the disease. Examples of the disease include diabetes, a neurodegenerative disease, arthritis, cancer, or an autoimmune disorder. The expression level can be determined at either the mRNA level or at the protein level.

Thus, one aspect relates to a method for identifying an agent that alters a function of an undifferentiated cell in an Lgr5+ SB cell population by contacting the cell with a test agent. A change in a function or gene expression of the cells in presence of the test agent as compared to the function in the absence of the test agent indicates that the test agent is an agent that alters the function of or the gene expression in the cells. The term "test agent" refers to any molecule that is being examined for an ability to alter a function of or gene expression in the cells. Although the method generally is used as a screening assay to identify previously unknown molecules that have a desired activity, the screening methods of the invention also can be used to confirm that an agent known to have a particular activity.

The function can be expression of gene that typically is expressed (or not expressed) in the cells, and the agent can alter the function by increasing or decreasing the level of expression of an expressed gene, or by turning on the expression of an unexpressed gene (e.g., inducing expression of lineage-specific antigen) in the cells.

In one embodiment, the agent that affects a function of the cells is one that induces differentiation of stem cells, thereby producing differentiated cells. Such differentiated cells can be multipotent human stem cells (e.g., hematopoietic stein cells) or can be terminally differentiated cells (e.g., muscle cells, neuronal cells, blood cells, connective tissue, and epithelial cells). As such, the method can be used to identify an agent that induces differentiation of stem cells in an Lgr5+ SB cell population to terminally differentiated cells including pancreatic beta cells, hepatocytes, cardiomyocytes, skeletal muscle cells, or any other cell types. Agents or compound thus-identified can be used to treat degenerative disorders, cancer or immune disorders.

The expression level can be determined at either the mRNA level or the protein level. Methods of measuring mRNA levels in a sample are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a sample are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and nanoparticles (e.g., Qdot™ supplied by the Quantum Dot Corporation, Palo Alto, Calif.). Other applicable methods include quantitative immunoprecipitation or complement fixation assays.

A test compound or agent can be any type of molecule, for example, a polynucleotide, a peptide, a peptidomimetic, peptoids such as vinylogous peptoids, a small organic molecule, or the like, and can act in any of various ways to alter a function of stem cells in an Lgr5+ SB cell population. For example, the test agent can act extracellularly by binding to a cell surface receptor expressed by the cells, thereby altering a function mediated by binding of a ligand that generally binds to and acts via the receptor. Alternatively, the test agent can be one that traverses the cell membrane, either passively or via an active transport mechanism, and acts within the cells to alter a function.

A peptide test agent can be any polymer of amino acids or amino acid analogs, and can vary from about three to four residues to hundreds or thousands. Peptide test agents can be prepared by chemical synthesis, or using methods of protein purification, followed by proteolysis and, if desired, further purification by chromatographic or electrophoretic methods, or can be expressed from an encoding polynucleotide. A peptide test agent can be based on a known peptide, for example, a naturally occurring peptide, but can vary from the naturally occurring sequence, for example, by containing one or more amino acid analogs.

A polynucleotide agent can be a sequence of two or more deoxyribonucleotides or ribonucleotides that are linked together by a phosphodiester bond. It can be RNA or DNA, which can be a gene or a portion thereof, a cDNA, an RNAi agent, a synthetic polydeoxy-ribonucleic acid sequence, or the like, and can be single stranded or double stranded, as well as a DNA/RNA hybrid. It can be a naturally occurring nucleic acid molecule, which can be isolated from a cell, as well as a synthetic molecule, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond. Such nucleotide analogs are well known in the art and commercially available, as are polynucleotides containing such nucleotide analogs (Pagratis et al., Nature Biotechnol. 15:68-73, 1997).

A polynucleotide test agent can be contacted with or introduced into stem cells in an Lgr5+ SB cell population using methods as disclosed herein or otherwise known in the art. Generally, but not necessarily, the polynucleotide is introduced into the cell, where it effects its function either directly, or following transcription or translation or both. For example, the polynucleotide can encode a peptide test agent, which is expressed in the cells and alters a function of the cells. A polynucleotide test agent also can be, or can encode, an antisense molecule, a ribozyme or a triplexing agent, which can be designed to target one or more specific target nucleic acid molecules.

Candidate agents or compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Lam, 1997. Anticancer Drug Des. 12:145. Examples of methods for the synthesis of molecular libraries can be found in, e.g., Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Felici 1991, J. Mol. Biol. 222:301-310; and U.S. Pat. No. 5,223,409).

Treating Degenerative Disorders

One can use the Lgr5+ SB cells disclosed herein for treating degenerative or inherited diseases.

To do so, one can isolate an Lgr5+ SB cell population from a patient, e.g., lacking a functional gene essential for proper development of a tissue or organ, One can then introduce into stem cells in the Lgr5+ SB cell population an expression nucleic acid vector encoding a functional version of the gene. The vector can be introduced into the stem cells via a variety of techniques, including calcium phosphate co-precipitation, DEAE-dextran-mediated transfection, lipofection, electroporation, microinjection, or virus-meditated techniques. Methods not affecting the pluripotency of the cells are preferred. Description of such techniques can be found in, e.g., U.S. Pat. Nos. 7,422,736 and 5,591,625. After delivering the functional gene into the stem cells, one can transplant them back into the patient using method known in the art. As the stem cells are produced from the patient, the treatment does not cause immune rejection.

Alternatively, one can make universal donor cells from an Lgr5+ SB cell population prepared from a healthy subject. The method for making universal donor cells are known in the art and that for making universal pluripotent stem cells from an Lgr5+ SB cell population is described below.

Under proper conditions, the transplanted stem cells can develop into a functional tissue or organ. To facilitate this development, the patient may be administered with factors to induce the development of the cells. Such factors can be small molecule compounds, peptides, and nucleic acids. Examples include, but are not limited to, transforming growth factor β, bone morphogenic proteins, and nerve growth factor.

The universal pluripotent stem cells are also useful for studying development or differentiation mechanisms of lineage development and differentiation. One can identify conditions for inducing the development of totipoent pluripotent stem cells into a specific tissue or organ using such cells as a model system. Further, one can isolate genes that play roles during the development using differential cDNA screening known in the art. One can prepare a cDNA library from the cells that have been induced to develop into a certain lineage, e.g., neuro-glial lineage described above. The library can then be used to isolate and study genes differentially expressed. These isolated genes can be further studied to define their roles in respective processes. The related techniques are known in the art. See e.g., U.S. Pat. No. 7,422,736. The pluripotent stem cells can also be used to develop into organs or clones of the animals using the methods known in the art. Accordingly, these cells are valuable for the pet and livestock industries, and can be used to preserve endangered animals.

As mentioned above, described herein is a method of treating a degenerative disease in a subject. The method includes administering to a subject in need thereof an effective amount of the above-described Lgr5+ SB stem cells. In one embodiment, at least one of these cells can include a recombinant nucleic acid. The recombinant nucleic acid can encode a polypeptide and the stem cell can contain an mRNA encoding the polypeptide. The degenerative disease can be, e.g., diabetes, a neurodegenerative disorder, and arthritis. Examples of a neurodegenerative disorder include Parkinson's disease, Alzheimer's disease, Huntington's disease, and ALS.

A subject to be treated for one of the above-described disorders can be identified by standard diagnosing techniques for that particular disorder. "Treating" refers to administration of a composition (e.g., a cell composition) to a subject, who is suffering from or is at risk for developing that disorder, with the purpose to cure, alleviate, relieve, remedy, delay the onset of, prevent, or ameliorate the disorder, the symptom of the disorder, the disease state secondary to the disorder, or the predisposition toward the damage/disorder. An "effective amount" refers to an amount of the composition that is capable of producing a medically desirable result in a treated subject. The treatment method can be performed alone or in conjunction with other drugs or therapies.

A degenerative disease refers to a disorder where the function or structure of an affected tissue or organ progressively deteriorate over time, whether due to genetic defects, injury, lack of proper cell differentiation (e.g., that in cell proliferative disorders), normal bodily wear, or lifestyle choices. Examples of degenerative diseases include neurodegenerative diseases (e.g., Alzheimer's disease, Parkinson disease, Huntington's disease, multiple sclerosis, and ALS); other nervous system disorders (e.g., transverse myelitis, demyelination occurring after trauma to the brain or spinal cord, acute brain injury, head trauma, spinal cord injury, peripheral nerve injury, ischaemic brain injury, hereditary myelin disorder of the CNS, epilepsy, perinatal asphxia, asphyxia, anoxia, status epilepticus, Shy-Drager syndrome, autism, and stroke); muscle-degenerative diseases (e.g., muscular dystrophy, fibromyalgia, myopathy, dermatomyositis, polymyositis, rhabdomyolysis, and myocarditis); cancer or a condition resulting from related cancers therapy (e.g., chemotherapy); metabolic disorders (e.g., diabetes/ diabetes mellitus and Niemann Pick disease); autoimmune or inflammation related disorders (e.g., erythematosis, inflammatory bowel disease (IBD), postatitis, osteoarthritis, osteoporosis, rheumatoid arthritis, lupus, diabetes, and asthma); ocular disorders (e.g., glaucoma, retinitis pigmentosa, Norrie disease, and macular degeneration); heart and circulatory disorders (e.g., atherosclerosis, heart failure myocardial infarction, and cardiovascular disease); blood disorders (e.g., Wiscott Aldrich syndrome); gastrointestinal disease; kidney disease; liver disease; lung disease; adrenal disorders (e.g., Addison's disease); a condition resulting from an injury (e.g., a burn, a stroke, damaged tissue, including flesh wounds, age damaged cells, and age damaged tissue); a condition associated with aging (e.g., hair loss, including male pattern baldness and alopecia areata); viral conditions (e.g., hepatitis C infection and acquired immune deficiency disorder); and any other disorder that an organ transplant or stem cells can be used to restore, regenerate, or otherwise ameliorate signs and/or symptoms associated with the disorder. The method of this invention can be used in treating erectile dysfunction and in plastic surgery or breast implantation for female.

The above-described Lgr5+ SB stem cells can be used in a method of treating brain or CNS tissue damage or alleviate the symptom of the disorder in a subject. The method includes identifying a subject suffering from or being at risk for developing brain tissue damage. The subject can be a human or a non-human mammal, such as a cat, a dog, or a horse. Examples of the brain tissue damage include those caused by a cerebral ischemia (e.g., chronic stroke) or a neurodegenerative disease (e.g., Parkinson's disease, Alzheimer's disease, spinocerebellar disease, and Huntington's disease). A subject to be treated can be identified by standard techniques for diagnosing the conditions or disorders of interest. The treatment method entails administering to a subject in need thereof an effective amount of the above-described stem cells or active agents/compounds.

The therapeutic effects of the Lgr5+ SB stem cells can be accessed according to standard methods. For example, to confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without stem cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is a useful indicator for following the effect of stem cell transplantation after cerebral ischemia.

Gene Therapy

The stem cells described herein can be used to express exogenous, recombinant polypeptide. Thus, within the scope of this invention are such stem cells, which contain a recombinant nucleic acid. The recombinant nucleic acid can encode a polypeptide and the stem cells can contain an mRNA encoding the polypeptide.

These stem cells can be genetically manipulated so that they do not express the beta2-microglobulin gene or do not express one or more proteins encoded by the class I major histocompatibility complex (MHC) genes that elicit a T lymphocyte mediated reaction against the cell. These cells can be used as universal donor cells since they do not lead to host rejections of grafts.

Accordingly, described herein is a method for introducing a heterologous nucleic acid in a subject. The method includes the steps of obtaining the above-described stem cells, where at least one of the stem cells includes a heterologous nucleic acid, and administering the cell into a subject in need thereof. The heterologous nucleic acid can encode a polypeptide.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous protein indicates that the protein comprises two or more subsequences that are not found in the same relationship to each other in nature (e.g., a "fusion protein," where the two subsequences are encoded by a single nucleic acid sequence). Such protein can be generated by recombinant techniques.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The above-described stem cells and methods can be used in various gene therapy methods known in the art. Gene therapy includes both ex vivo and in vivo techniques. Specifically, the above-described stem cells can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). Alternatively, cells may be cultured on a suitable biocompatible support and transplanted into a patient. The engineered cells are typically autologous so as to circumvent xenogeneic or allotypic rejection. Such ex vivo methods are well known in the art.

The cells can be engineered by administration of the oligonucleotide or nucleic acid molecule using techniques known in the art. For example, oligonucleotides and other nucleic acid molecules can be administered by direct injection of a "naked" nucleic acid molecule (U.S. Pat. No. 5,679,647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837, 533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis, which can be used to target cell types specifically expressing the receptors.

A nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor. In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and subsequent incorporation within host cell DNA for expression by homologous recombination known in the art.

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/QFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

The expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

Compositions

Pharmaceutical compositions containing the above-described Lgr5+ SB cells with or without other active agents can be prepared by mixing a therapeutically effective amount of the cells or active agents/compounds, and, optionally other active substance, with a pharmaceutically acceptable carrier. The carrier can have different forms, depending on the route of administration. Examples of other active substance include active compounds known or identified by the screening method of described above.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the above-described stem cells can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The above-described Lgr5+ SB stem cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art. In all of the above-described methods, the stem cells can be administered to a subject at $1 \times 10^4$ to $1 \times 10^{10}$/time.

Evaluation Method

The Lgr5+ SB stem cells and methods disclosed herein can be used to evaluate a subject. Generally, a young healthy subject has a relative higher percentage of stem cells. It has been shown that the numbers or parentages of these cells decrease as the subject ages or due to genetic defect or expose to unfavorable environmental factors. This decrease compromises the subject's stem-cell related abilities, including ability to repair tissue after an injury.

These changes can be used to evaluate a subject risk for having an ageing related disorder. For example, if a subject has higher-than-average level, he or she has excellent ability to repair tissue after an injury and high risk of develop cancer. In other words, a high level of the above-mentioned stem cells in a sample from the subject indicates that a subject has a young development status with (1) a better ability to repair tissue damage, to recover from an injury, and to defend pathogens and (2) lower probabilities of developing an autoimmune disease, a cardiovascular disease, diabetes, and other disorders associated with ageing. On the other hand, such a higher level is positively correlated with a higher risk of having cancer.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety. Further, any mechanism proposed below does not in any way restrict the scope of the claims.

EXAMPLE 1

Isolation of an Lgr5+ SB cell population

Human blood samples and bone marrow samples were obtained and placed in an anti-clotting EDTA tube or heparin tube as described previously and above. See US2012/0034194. After incubating the tube for 6 to 48 hours at 4° C., the sample separated into two layers.

The bottom layer, which appeared red, consisted almost entirely of red (RBC) and white blood cells while the top layer contained SB cells. Since the SB cells were in the top layer, we assumed that they were smaller than the 6 μm-wide RBCS. This separation narrowed the identity of the cells in the top layer to SB cells, platelets, and extracellular vesicles, including microparticles, microvesicles, and apoptotic bodies, as they all fall under this size restriction. Platelets and extracellular vesicles showed up as negative under DAPI or SYTO staining since they lack nuclei. Similarly, apoptotic bodies lack integral chromosomes, producing a negative FISH chromosome stain. Our results indicated that an average of less than 10% of the top-layer cells were DAPI positive; such DAPI positive cells excluded platelets and extracellular vesicles. To verify the presence of integral chromosome structures, we performed the FISH Y chromosome staining for SB cells. SB cells from a male donor were seeded at the top of a transwell and large stromal cells from a female donor were plated at the bottom. After two to three days of incubation, the SB cells were passed through the 5 μm filters of the transwell. The cells from the male donor were targeted using Y-chromosome fluorescence. Around the big stromal cells, one small cell was positive for both the FISH and DAPI stainings, indicating that SB cells contain an integral chromosome structure. The negative Annexin V staining of the SB cells further confirms their identity. Thus, the SB cells were not apoptotic bodies, platelets or extracellular vesicles.

To additionally characterize the SB mixture (i.e., the top layer), samples were analyzed using flow cytometry. By comparing the non-purified blood sample with bead sizes as a reference, we found that the size of gate G2 was smaller than 1 μm, indicating that this region consisted mostly of microparticles or microvesicles. Gate G3, which included cells with a diameter greater than 1 μm, included three populations: G4, G5, and G6. Analysis using the RBC lysis buffer indicated the presence of RBCs in the G6 region, where 99.6% of the cells in this region were confirmed as CD235a-positive and negative for SYTQ nucleus. The cells in the G5 region were also larger than RBCs (G6) and were presumed to be white blood cells (WBCs) because these cells stained positive for CD11b.

The cells of the SB mixture were present in the G4 region, confirming that SB cells were smaller than RBCs. The post-purification procedure removed nearly all of the RBCs (G6) and WBCs (G5) in the human blood and bone marrow samples. Only in G4, more than 80% of the cells derived from human blood stained positive for CD9, a platelet marker; nearly all of these cells were captured by the P1 region. CD9 negative cells comprised 10-20% of the G4 population and were captured in the P2 region. Gating in this region revealed that 78% of the cells were positive for SYTO nucleus staining, and 61.7% of the cells were positive for Lgr5. Cells from 30 bone marrow and 70 peripheral blood samples were analyzed.

Lgr5+ cells were also found to be Oct4+ and Nanog+, and CD133−, CD66e−, Sox2−, CD4−, CD8−, CD9−, CD10−, CD11–, CD16–, CD17–, CD18–, CD19–, CD20–, CD21–, CD31–, CD42–, CD63–, CD34–, Lin–, CD38–, CD90–, CD45–, and CD349–.

The SB mixture was also investigated for the possible presence of other small stem cells, i.e., blastomere-like stem cells (BLSCs), and very-small embryonic-like stem cells (VSELs), using the CD66e and CD133 markers, respectively. Less than 1% of the cells in the SB mixture expressed either CD66e or CD133.

EXAMPLE 2

Proliferation and Differentiation of Lgr5+ SB cells

Lgr5+ SB cells were isolated from an SB cell population using two methods: FACSorting and magnetic enrichment. The PE Selection Kit (StemCell Technologies, catalog number 18551) was used to isolate the Lgr5+ cells. The SB cell population was incubated with a PE selection cocktail (using an Lgr5-PE antibody) for 15 minutes and magnetic nanoparticles for 10 minutes at room temperature (RT). The mixture was placed into the magnet and set aside for 5 minutes at RT. The supernatant was then discarded, and the cells were plated for further culturing. Alternatively, cells of the SB population were stained with Lgr5-PE and isolated via FACSorting using the BD FACSAria at the UCLA Flow Cytometry Core Facility.

These purified Lgr5+ cells were collected and assayed in vitro. After a period of culture, the cells grew to between 6 and 25 µm in diameter. This proliferation and size increase suggested the presence of small stem cells.

The Lgr5+ cells were cultured in different types of differentiation media, which were changed every 2-3 days. As previously described, for hepatocyte differentiation, the cells were cultured in three different types of media: DMEM high glucose medium with 3% horse serum, 1× antibiotic, 1× L-glutamine, and 5 ng/mL activin for 4 days; DMEM high glucose medium with 3% horse serum, 1× antibiotic, 1× L-glutamine, 20 ng/mL bFGF, and 5 ng/mL hBMP2 for 10 days; and Hepato ZYME SFM (from Life Technologies Gibco) with 2% horse serum, 1× antibiotic, 10 ng/mL HGF, 1×10–8 M sex, and OSM 10 ng/mL for 10 to 15 days. See, Talens-Visconti et al., World J Gastroenterol 12: 5834-5845. For neurogenic, osteogenic, and adipogenic differentiation, the cells were grown in neuronal, osteocytic, and adipocytic differentiation media, respectively, which were obtained from Life Technologies and used according to the protocols provided by the manufacturer. For osteocyte and adipocyte staining/detection, osteocyte (Millipore, catalog number ECM815) and adipocyte detection kits were used. This in vitro characterization was performed four times (three times with cells purified using the StemCell PE isolation kit and one time with cells purified using FACSorting).

To test for mesoderm differentiation, the cells were cultured in adipogenesis medium. Oil-Red O staining indicated significant increases in the number of adipocytes compared to the negative control. The cells were also converted into hepatocytes and endoderm cells in the hepatocyte differentiation media. These cells secreted 50 ng/ml albumin into the medium and expressed several hepatocyte-specific genes, such as albumin, FoxA2, and alpha-fetoprotein. To investigate the potential of ectoderm differentiation, the cells were similarly cultured in neuronal differentiation medium. Neurofilament and MAPT expression increased with each successive day in culture. The results from the ICC neurofilament staining also confirmed the cells' potential to neuronally differentiate. These data show that the purified Lgr5+ cells were able to differentiate in vitro into the three different germ layer cells.

EXAMPLE 3

Engraftment of Lgr5+ SB Cells in SCID Mice

An in vivo tracking assay with isolated Lgr5+ SB cells was performed. Lgr5+ SB cells from a human male bone marrow sample were purified and re-suspended in PBS with 5% human albumin for injection at Charles River Laboratories. Two groups of six female SCID mice (6-8 weeks old) received a sub-lethal (2Gγ) gamma-irradiation prior to injection. Each mouse was injected twice with $1 \times 10^5$ cells, first immediately after the radiation and once more 24 hours later. The negative control group consisted of mice injected with PBS. Tissues were collected at 60 days after the first injection. Half of the tissues were prepared as frozen sections by Charles River Laboratories, and the remaining tissues were sent to StemBios in RNAlater reagent for gene expression analysis at the RNA level. The FISH technique, which employs fluorescent human specific Y-chromosome probes, was used to detect human cells in vivo.

The use of SCID mice, lacking T cells and B cells, ensured that the sub-lethal irradiation would eliminate NK cells, which could led to rejection of the Lgr5+ SB cells. In addition, such irradiation would create an injury signal in the mouse body, which may be important in the guidance of stem cells to the injury site for repair.

As observed in the collected brain, liver, and muscle tissue samples, cells that were cyc3-DAPI double-positive had originated from humans. These results were consistent for all six mice in the experimental group, suggesting that the injury signal guided the migration of the Lgr5+ SB cells to the injury site. To determine whether the cells that migrated to the organs were capable of differentiating, RT-PCR was performed. Beta-actin, α1-anti-trypsin, myogenic factor 4, and Tau gene expression were assessed in these organs. In this assay, primers against mouse beta-actin served as the positive control and primers for the liver, brain, and skeletal muscle were human-specific. The results demonstrated that human Lgr5+ SB cells resided in the mouse brain, liver, and skeletal muscles and differentiated into hepatocytes, neurons, and skeletal muscles in the host. These data were also consistent for all six mice in the experimental group.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments have been described. Nevertheless, it will be understood that various modifications may be made without departing from the spirit and scope of the invention. Accordingly, other embodiments are within the scope of the following claims.

What is claimed is:
1. A method of preparing a mixture, comprising:
incubating a tissue sample from a subject with a divalent cation chelating agent until said tissue sample is sepa- rated into an upper layer and a lower layer, wherein said tissue sample contains a plurality of cells; and collecting the upper layer, wherein the upper layer contains somatic stem cells that are 2 to less than 6 micrometers in size and Lgr5+, whereby the mixture is prepared.

2. The method of claim 1, wherein said divalent cation chelating agent comprises EDTA.

3. The method of claim 1, wherein said divalent cation chelating agent comprises citrate.

4. The method of claim 2, wherein said tissue sample is incubated with said divalent cation chelating agent for 6 to 48 hours.

5. The method of claim 4, wherein said tissue sample is incubated with said divalent cation chelating agent at a temperature of 4° C.

6. The method of claim 1, wherein less than 1% of cells in the upper layer expresses CD133.

7. The method of claim 1, wherein the upper layer contains blastomere-like stem cells (BLSCs).

8. The method of claim 1, wherein said somatic stem cells are CD9− and CD349−.

9. The method of claim 1, wherein said somatic stem cells are Oct4+, Nanog+, CD133−, and CD66e−.

10. The method of claim 5, wherein said tissue sample is a blood sample or bone marrow sample.

11. The method of claim 10, further comprising, after the collecting step, adding a pharmaceutical acceptable carrier to the collected upper layer to produce the mixture.

12. The method of claim 11, wherein the pharmaceutical acceptable carrier is saline.

13. A mixture comprising somatic stem cells that are 2 to less than 6 micrometers in size and Lgr5+, wherein the mixture is prepared by a method including:

incubating a bone marrow or blood sample from a subject with EDTA for 6 to 48 hours at 4° C. until the sample is separated into an upper layer and a lower layer; and collecting the upper layer, wherein the upper layer contains somatic stem cells that are 2 to less than 6 micrometers in size and Lgr5+, whereby the mixture is prepared.

14. The mixture of claim 13 further comprising blastomere-like stem cells (BLSCs).

15. The mixture of claim 13 further comprising very-small embryonic-like stem cells (VSELs).

16. The mixture of claim 13, wherein said somatic stem cells are CD9− and CD349−.

17. The mixture of claim 13, wherein said somatic stem cells are Oct4+, Nanog+, CD133−, and CD66e−.

18. The mixture of claim 13, wherein less than 1% of cells in said mixture expresses CD133.

19. The mixture of claim 13, further comprising a pharmaceutical acceptable carrier.

20. The mixture of claim 19, wherein the pharmaceutical acceptable carrier is saline.

* * * * *